(12) United States Patent
Mangosong

(10) Patent No.: US 6,267,751 B1
(45) Date of Patent: *Jul. 31, 2001

(54) SUCTION SUPPORT AND METHOD OF USE

(75) Inventor: Lorraine Mangosong, Palo Alto, CA (US)

(73) Assignee: Embol-X, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/411,483

(22) Filed: Oct. 1, 1999

Related U.S. Application Data

(63) Continuation of application No. 09/161,937, filed on Sep. 28, 1998, now Pat. No. 6,007,523.

(51) Int. Cl.$^7$ ................................................. A61M 25/00
(52) U.S. Cl. ........................ 604/284; 604/315; 178/898; 600/201
(58) Field of Search ..................... 604/284, 540, 604/534, 173–176, 264, 523, 313, 315; 600/201–205, 206, 208, 210; 128/897–899

(56) References Cited

U.S. PATENT DOCUMENTS

| | | | |
|---|---|---|---|
| 1,972,391 | 9/1934 | Morse | 600/211 |
| 4,053,984 | * 10/1977 | Moss . | |
| 4,072,153 | 2/1978 | Swartz | 604/284 |
| 4,309,994 | * 1/1982 | Grunwald . | |
| 4,547,187 | 10/1985 | Kelly | 604/49 |
| 4,687,471 | 8/1987 | Twardowski et al. | 604/175 |
| 4,883,474 | 11/1989 | Sheridan | 604/540 |
| 5,196,003 | * 3/1993 | Bilweis . | |
| 5,484,391 | * 1/1996 | Buckman, Jr. et al. . | |
| 5,727,569 | 3/1998 | Benetti et al. | 128/898 |
| 5,735,290 | * 4/1998 | Sterman et al. . | |
| 5,749,892 | * 5/1998 | Vierra et al. . | |
| 5,762,606 | 6/1998 | Minnich | 600/205 |
| 5,836,311 | 11/1998 | Borst et al. | 128/897 |
| 5,865,730 | * 2/1999 | Fox et al. . | |
| 5,885,271 | 3/1999 | Hamilton et al. | 606/1 |
| 5,891,017 | 4/1999 | Swindle et al. | 600/205 |
| 5,906,607 | * 5/1999 | Taylor et al. . | |
| 6,007,523 | * 12/1999 | Mangosong | 604/284 |
| 6,017,352 | * 1/2000 | Nash et al. . | |

FOREIGN PATENT DOCUMENTS

WO96/40354 * 12/1996 (WO) .

* cited by examiner

Primary Examiner—Richard K. Seidel
Assistant Examiner—LoAn H. Thanh
(74) Attorney, Agent, or Firm—Lyon & Lyon LLP

(57) ABSTRACT

The invention provides devices and methods for endoscopically cannulating the aorta, right atrium, and other body tissues to establish cardiopulmonary bypass for minimally invasive coronary artery bypass grafting surgery, and for other surgeries. After inserting the suction support through a minimal access port, the suction support having an arcuate member with suction ports provides countertraction to the aorta by creating a vacuum seal between its suction ports and the aorta, therefore facilitating aortic incision and cannulation. In one embodiment, the suction support allows aorta stabilization, incision, and insertion with an introducer to be achieved sequentially. Methods for using the devices herein are also disclosed.

9 Claims, 4 Drawing Sheets

SUCTION SUPPORT AND METHOD OF USE

This is a continuation of application Ser. No. 09/161,937 filed Sep. 28, 1998, now U.S. Pat. No. 6,007,523, the contents of which are expressly incorporated herein by reference.

FIELD OF THE INVENTION

The present invention relates generally to body tissue stabilization using a suction support system, and more particularly, relates to using the system to stabilize the aorta and right atrium by providing countertraction during minimally invasive cardiac surgery.

BACKGROUND OF THE INVENTION

Coronary artery bypass grafting (CABG) is a well-established procedure for patients with ischemic heart disease. However, significant mortality and morbidity still exists due to the use of cardiopulmonary bypass for circulating support and the traditional method of access by medium sternotomy. Minimally invasive surgical procedures using an endoscopic approach have been adopted in cardiac surgery in an attempt to make these procedures less invasive. In port-access approach, minimal access incisions are made in the intercostal space for insertion of various endoscopic instruments, and cardiopulmonary support is instituted through an extrathoracic approach.

The right atrium and the ascending aorta are often cannulated in preparation for cardiopulmonary bypass (CPB). In order to cannulate the right atrium and the aorta, incisions have to be made on these soft and pulsating tissues. It is difficult, however, to make such incisions because these tissues are moving during such procedures. Moreover, because the aorta, and other tissues, are soft and pliable, the aorta will compress when a device, such as a blade or cannula, presses against it. A need for devices and methods therefore exists to endoscopically assist the surgeon in stabilizing pliable and/or moving tissue by providing countertraction.

SUMMARY OF THE INVENTION

The present invention relates to an endoscopic stabilization device having an ability to hold a soft, moving body tissue in place while the tissue is being operated on. More particularly, this device is a suction support comprising an elongate tubular member having a proximal end, a distal end, and a lumen therebetween. An arcuate member is joined to the distal end of the tubular member and has a lumen which communicates with the lumen of the elongate member. A plurality of suction ports is disposed along the arcuate member and communicates with the lumen of the arcuate member. The proximal end of the suction support is adapted for attachment to a vacuum. The elongate member and the arcuate member are generally joined at an angle between 45° to 135°.

In an alternative embodiment, the suction support has an additional lumen attached along its elongate member for insertion of a surgical blade to incise the aorta or right atrium at its distal opening. A further alternative suction support has an additional lumen with a surgical blade which is mounted at its distal end and communicates with the proximal end. The blade is pushed forward to incise the atrium and the aorta, and retracted back into the lumen when manipulated at the proximal end. As a force is exerted on the aorta or atrium by probing the blade forward, a counter-force is exerted by the suction support, thereby stabilizing the moving aorta or atrium for a precise incision.

The present invention also provides methods for stabilizing a body tissue during surgery. The methods employ a suction support comprising an elongate member having a plurality of suction ports and joined to a distal end of the tubular member. The suction support is generally introduced into a patient's thoracic cavity through an incision, preferably an intercostal incision, and is positioned about a body tissue, such as the aorta or heart. Vacuum is applied to the lumen of the elongate tubular member wherein the body tissue becomes releasably engaged by the suction ports. The body tissue is released from the suction port by removing the vacuum. During minimally invasive CABG, the right atrium and ascending aorta are the body tissues of interest requiring stabilization before cannulation or CPB.

The present invention also provides methods for making an incision on the body tissue for cannulation after stabilization by the suction support. The surgical blade, optionally contained in a lumen, can be manipulated from the proximal end to incise the aorta or the right atrium while the suction support provides countertraction.

In an alternative embodiment wherein an introducer is attached to the suction support, the suction support also provides countertraction on the aorta and right atrium during introducer insertion. The steps of stabilizing, incising a body tissue and inserting an introducer can be achieved sequentially on one track, therefore providing a simplified surgical method for cannulation for CPB. In a still further embodiment, the suction support can be attached to a trocar for visualization into a patient's chest cavity.

DETAILED DESCRIPTION OF THE INVENTION

The devices and methods disclosed herein facilitate stabilization of the aorta and right atrium using endoscopic techniques. In addition, the devices and methods facilitate incision and cannulation on these body tissues in preparation for CPB. In this way, the devices and methods allow CPB to be established without the need for a medium sternotomy or other form of gross tracheotomy and without the need for a peripheral arterial access. Once the patient is on CPB with the heart arrested, a variety of thorascopic, endovascular, or open surgical procedures may be performed, including coronary artery bypass grafting, heart valve repair and replacement, septal defect repair, pulmonary thrombectomy, removal of atrial myxoma, patent foramen ovale closure, aneurysm repair, atherectomy, correction of congenital defects, and other interventional procedures.

Figure 1:
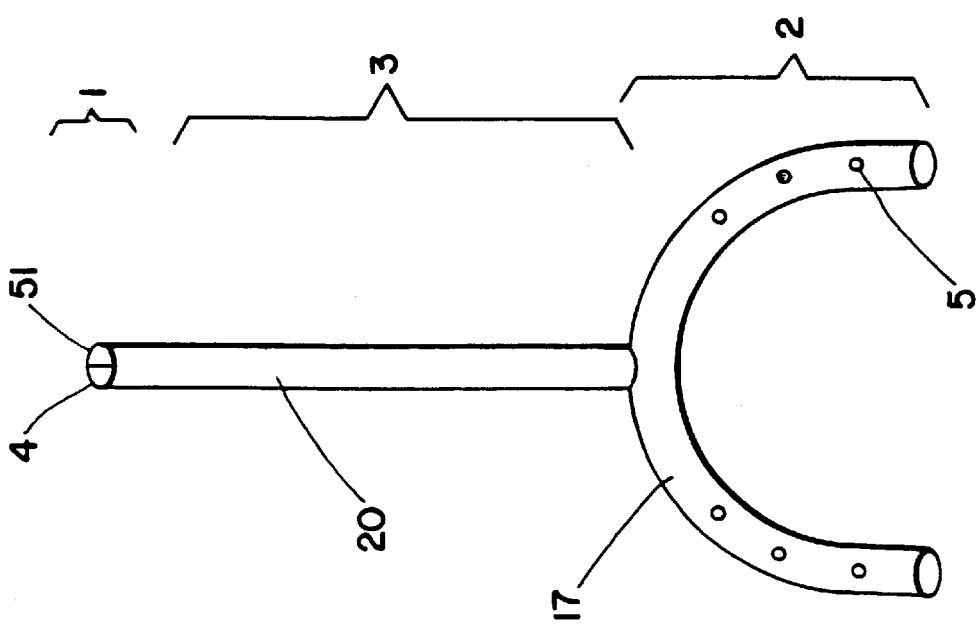
FIG. 1 depicts a frontal view of a preferred embodiment of the suction support.

FIG. 1 depicts a frontal view of a preferred embodiment of a suction support. The suction support has elongate member 20 which includes proximal end 1, and transition region 3. Transition region 3 is connected to distal region 2 which comprises arcuate member 17. In this embodiment, the proximal end has lumen 4 which can be round, oval, or other suitable shapes, and can be connected to a vacuum suction pump. In certain embodiments, the proximal end will include a second lumen 51 carried by the elongate member. Arcuate member 17 has a plurality of suction ports 5 on its arms, between 3 and 10 preferably 5.

The length of elongate member 20 will generally be between 5 and 40 centimeters, preferably 25 centimeters. The cross-sectional diameter of elongate member 20 will generally be between 0.2 centimeters to 1.5 centimeters, preferably 0.7 centimeters. The width of arcuate member 17 will generally be between 0.5 to 3.0 centimeters, preferably 1.5 centimeters with the width of its arms generally being between 0.2 to 1.0 centimeter, preferably 0.4 centimeters. Suction port 5 will commonly have an opening diameter of 0.3 to 10 millimeters, typically 0.7 millimeters. The arcuate member can be joined to the elongate member at an angle ranging from 45° to 135°. The foregoing ranges are set forth solely for the purpose of illustrating typical device dimensions. The actual dimension of a device constructed according to the principle of the present invention may obviously vary outside the listed ranges without departing from those basic principles.

Figure 2:
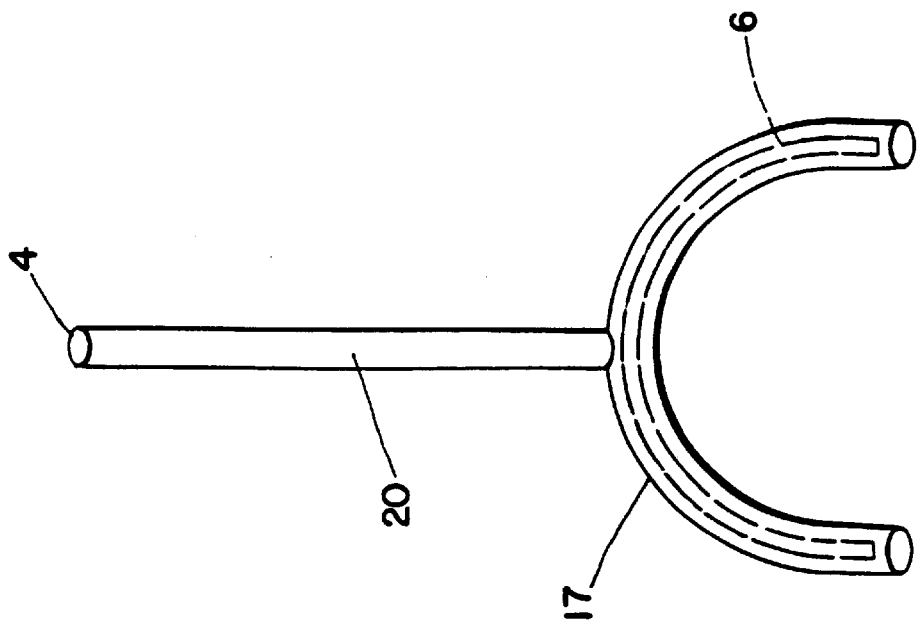
FIG. 2 depicts a frontal view of an alternative embodiment of the suction support, in which the arcuate member contains a continuous slot.

FIG. 2 depicts an alternative embodiment of the suction support, in which the arcuate member contains a continuous slot. Continuous slot 6 communicates with the lumen of the arcuate member, which in turn communicates with lumen 4 of elongate member 20. This embodiment may provide a better vacuum seal between the arcuate member and a body tissue.

Figure 3B:
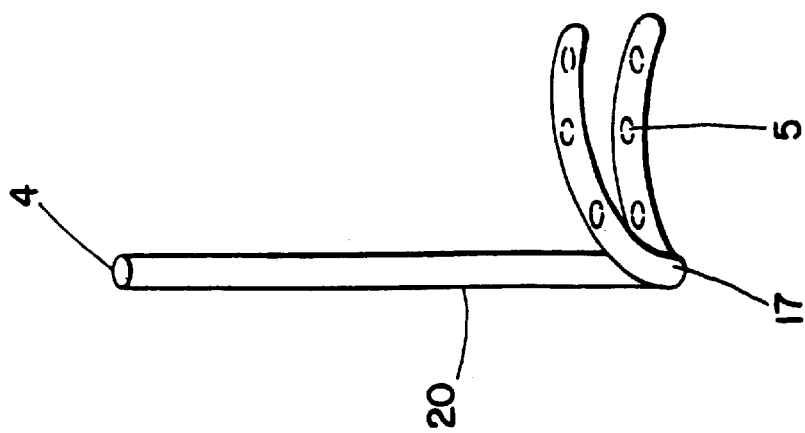
FIG. 3B depicts a lateral view of a suction support wherein the elongate member and the arcuate member are joined at an acute angle.
Figure 3A:
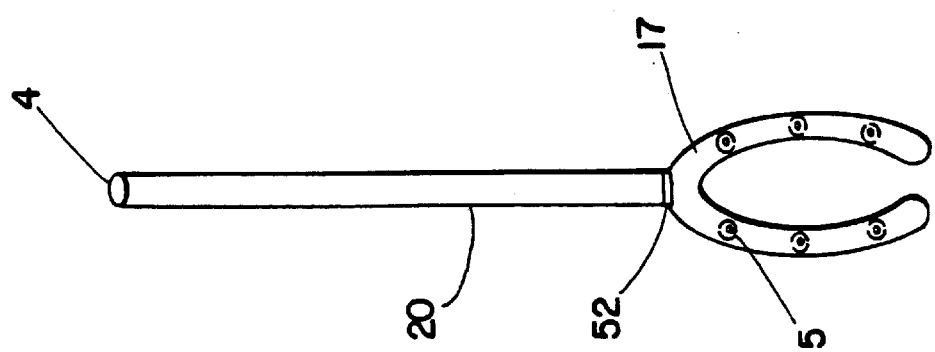
FIG. 3A depicts a lateral view of a suction support wherein the elongate member and the arcuate member are joined at a 180° angle.
Figure 3:
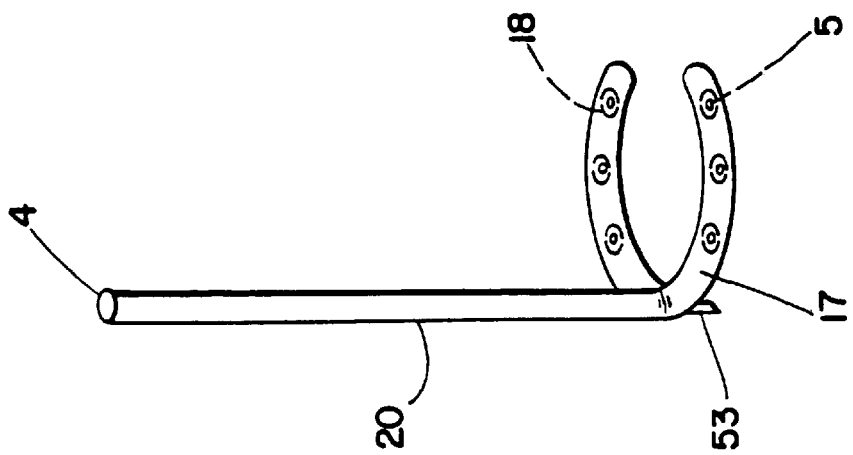
FIG. 3 depicts a lateral view of a suction support wherein the elongate member and the arcuate member are joined at approximately a 90° angle.

FIG. 3 depicts a lateral view of a suction support wherein elongate member 20 and arcuate member 17 are joined at approximately a 90° angle. In this embodiment, the arcuate member has each of its suction ports positioned at the center of a suction cup. Suction cups 18 may provide a better seal between the suction supports and the body tissue with vacuum. In certain embodiments, the distal end of elongate member 20 will include a rectractable blade 53.

FIG. 3A depicts a lateral view of a suction support wherein elongate member 20 and arcuate member 17 are joined pivotally at an angle which is adjustable (here shown at a 180° angle). This embodiment is advantageous in that it can be easily introduced through a small incision or access port. The arcuate member and the elongate member are joined at a pivot, or can be made malleable, so that they are joined at an angle which is adjustable. The suction support may further include a rotating locking mechanism 52 to secure the elongate member and the arcuate member at a desired angle, obtained after adjustment (such as the approximate 90° angle shown in FIG. 3).

FIG. 3B depicts a lateral view of a suction support wherein the elongate member and the arcuate member are joined at a less than 90° angle. Each arm of arcuate member 17 is constructed with a slight curvature (concave) to conform to the curvature of an aorta, thereby providing better contact between the suction support and the aorta.

Figure 4:
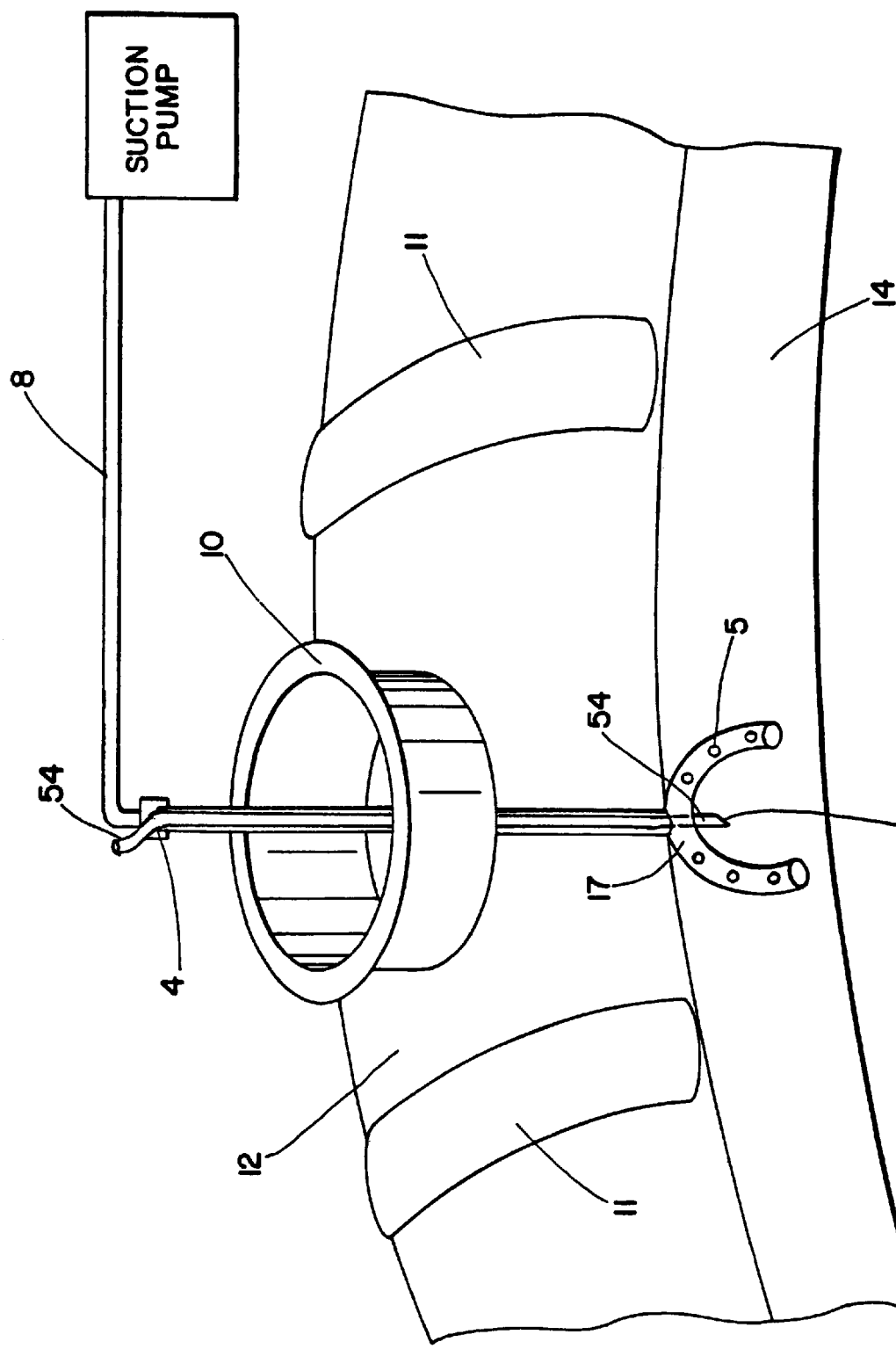
FIG. 4 depicts a method of stabilizing the aorta using suction support through a minimal access port.
Figure 5:
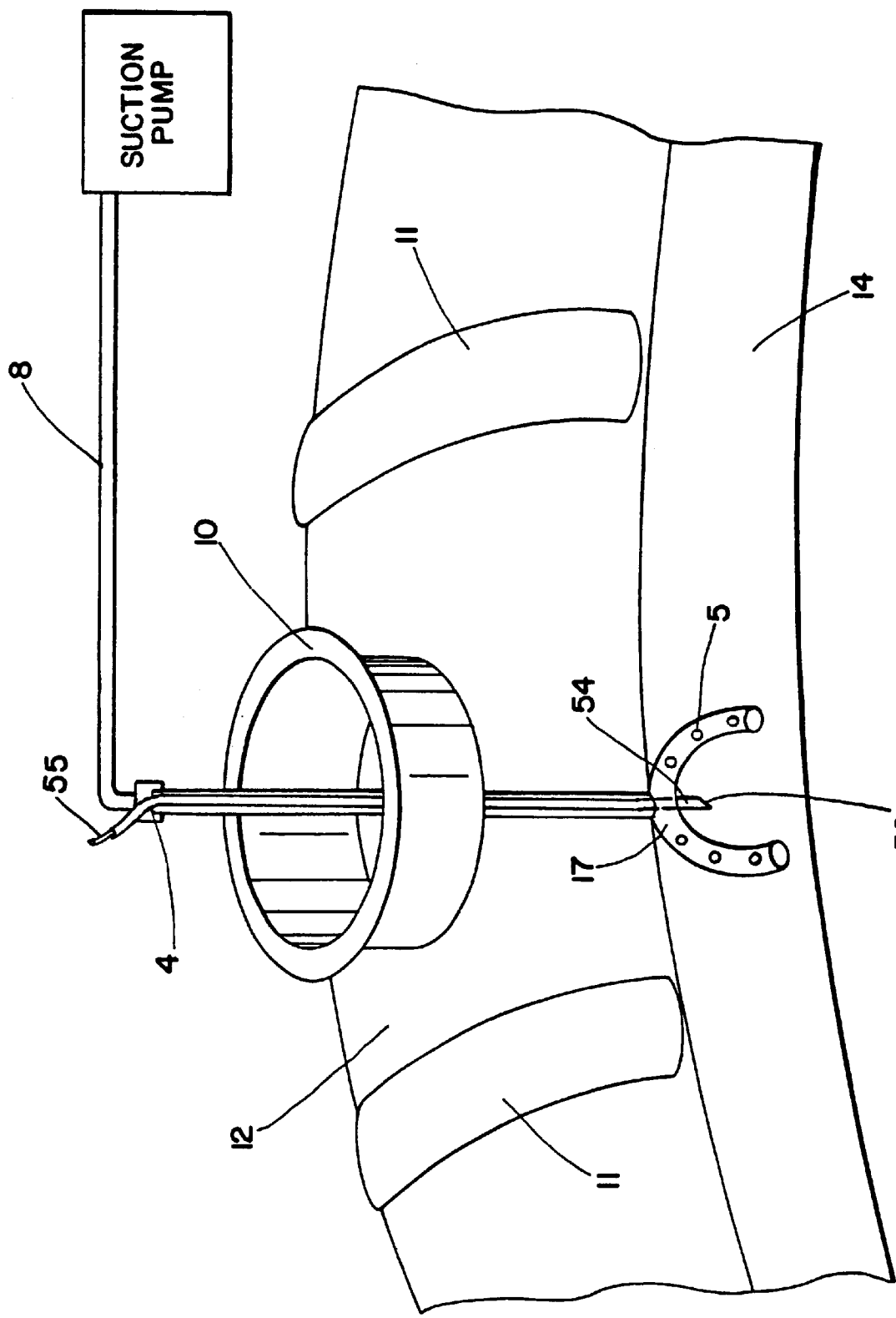
FIG. 5 depicts a method of cannulation using suction support through a minimal access port.

FIG. 4 depicts a method of stabilizing the aorta using a suction support through a minimal access port. Access port 10 is situated in intercostal space 12 between ribs 11. The suction support is inserted through access port 10 and makes contact with the outer surface of aorta 14 by its arcuate member 17. After the suction support is connected through connector 4 to a suction pump by connecting tubing 8, vacuum is applied at between 10 to 40 centimeter negative water pressure to create a seal between arcuate member 17 and the aorta. The suction support therefore stabilizes the pulsating aorta to allow incision 30 to be made by providing countertraction to the aorta. In certain embodiments, the elongate member of the suction support will carry an introducer 54 which provides a passage for instruments through incision 30, and along the same track as the elongate member.

The suction supports and methods disclosed herein are particularly useful in minimally invasive CABG surgery where port access approach is used. As described above, the suction support is inserted through a minimal access port situated in the intercostal space to make contact with the ascending aorta or the right atrium. The suction support, when under vacuum, will provide countertraction to the pulsating aorta or the right atrium. This allows the surgeon to make a precise incision on these body tissues, and enables an arterial or venous cannula to be inserted. The arterial cannula is inserted into the ascending aorta to transport oxygenated blood from the CPB machine while the venous cannula is inserted into the right atrium to transport the deoxygenated blood to the CPB machine. After the cannula is inserted, CPB is initiated, vacuum may be released, and the suction support may be removed. The surgeon then proceeds with the revascularization of the heart.

In addition to minimally invasive CABG surgery, the suction support devices herein can be employed in a similar fashion described above in a variety of cardiothoracic surgeries, including thoracic aortic aneurysm repair, septal defect repair, and valvular repair where CPB is indicated. The suction support may also assist in providing countertraction and/or stabilizing and incising body tissue in other endoscopic procedures, such as abdominal aortic aneurysm repair, laparoscopic cholecystectomy, laparoscopic oophorectomy and ovarian cyst removal.

Although the foregoing invention has, for purposes for clarity of understanding, been described in some detail by way of illustration and example, it will be obvious that certain changes and modifications may be practiced which will still fall within the scope of the appended claims.

What is claimed is:

1. A method for stabilizing a cardiac tissue during surgery, comprising the steps of:
    providing a suction support comprising an elongate tubular member having a lumen, and an arcuate member having at least one suction port and joined to a distal end of the tubular member;
    introducing the suction support into a patient's thoracic cavity through an incision;
    positioning the suction support about a cardiac tissue;
    applying a vacuum to the lumen of the elongate tubular member, wherein the cardiac tissue is releasably engaged by the suction port;
    making an incision on the cardiac tissue using a blade deployed through a lumen of the elongate tubular member; and
    inserting a cannula through the incision, wherein the cardiac tissue is stabilized by the suction support during insertion of the cannula without traumatizing the cardiac tissue.

2. The method of claim 1, wherein the cardiac tissue is an artery.

3. The method of claim 2, wherein the artery is an aorta.

4. The method of claim 1, wherein the cardiac tissue is an atrium.

5. The method of claim 1, wherein the cardiac tissue is a vein.

6. The method of claim 1, wherein the cardiac tissue includes a coronary artery.

7. The method of claim 1, further comprising the step of establishing cardiopulmonary bypass.

8. The method of claim 1, further comprising the step of performing coronary artery bypass grafting.

9. The method of claim 1, wherein the blade is deployed through a distal end of the elongate tubular member.

\* \* \* \* \*